United States Patent
Stumber et al.

(10) Patent No.: US 9,034,162 B2
(45) Date of Patent: May 19, 2015

(54) MICROFLUIDIC CELL

(75) Inventors: Michael Stumber, Korntal-Muenchingen (DE); Martina Daub, Weissach (DE); Jochen Rupp, Stuttgart (DE); Massimo Kubon, Muensingen-Rietheim (DE); Peter Rothacher, Bruchsal (DE); Meike Moschallski, Reutlingen-Ohmenhausen (DE); Martin Stelzle, Reutlingen (DE); Christian Dorrer, Stuttgart (DE)

(73) Assignee: ROBERT BOSCH GMBH, Stuttgart (DE)

(*) Notice: Subject to any disclaimer, the term of this patent is extended or adjusted under 35 U.S.C. 154(b) by 0 days.

(21) Appl. No.: 12/853,906

(22) Filed: Aug. 10, 2010

(65) Prior Publication Data

US 2011/0139620 A1 Jun. 16, 2011

(30) Foreign Application Priority Data

Aug. 13, 2009 (DE) .................. 10 2009 028 493

(51) Int. Cl.
*B03C 5/02* (2006.01)
*B01F 5/06* (2006.01)
*B01F 13/00* (2006.01)
*B01L 3/00* (2006.01)
*B03C 5/00* (2006.01)
*C12M 3/06* (2006.01)
*C12M 1/00* (2006.01)

(52) U.S. Cl.
CPC ................. *B03C 5/026* (2013.01); *B01F 5/061* (2013.01); *B01F 13/0076* (2013.01); *B01F 2005/0621* (2013.01); *B01F 2005/0636* (2013.01); *B01L 3/502753* (2013.01); *B01L 2200/0668* (2013.01); *B01L 2400/0424* (2013.01); *B03C 5/005* (2013.01); *C12M 23/16* (2013.01); *C12M 47/02* (2013.01); *C12M 47/04* (2013.01)

(58) Field of Classification Search
CPC ................... B01L 3/50273; B03C 5/00–5/005
USPC .................................. 204/450–470, 606–650
See application file for complete search history.

(56) References Cited

U.S. PATENT DOCUMENTS

| | | | | |
|---|---|---|---|---|
| 7,547,380 | B2* | 6/2009 | Velev | 204/547 |
| 2007/0125650 | A1* | 6/2007 | Scurati et al. | 204/547 |
| 2008/0008911 | A1* | 1/2008 | Stroock et al. | 429/13 |
| 2008/0283401 | A1* | 11/2008 | Peach | 204/547 |

OTHER PUBLICATIONS

Lee, Hsu-Yi, Woldman, Joel, Optimizing Micromixer Design for Enhancing Dielectrophoretic Microconcentrator Performance, 2007, Anal. Chem., 79, 1833-1839.*

* cited by examiner

*Primary Examiner* — Bach Dinh
(74) *Attorney, Agent, or Firm* — Kenyon & Kenyon LLP

(57) ABSTRACT

A microfluidic cell for the dielectrophoretic separation, accumulation, and/or lysis of polarizable bioparticles, including an interdigital electrode system composed of two electrode groups having interdigitated electrodes, and a micromixer having microchannels and microelevations. The interdigital electrode system and the micromixer are situated on the same side of the cell to improve the separation, accumulation, and/or lysis characteristics. Moreover, also described is a microfluidic system which includes such a microfluidic cell, and use thereof, and a method for separating, accumulating, and/or lysing polarizable bioparticles.

16 Claims, 11 Drawing Sheets

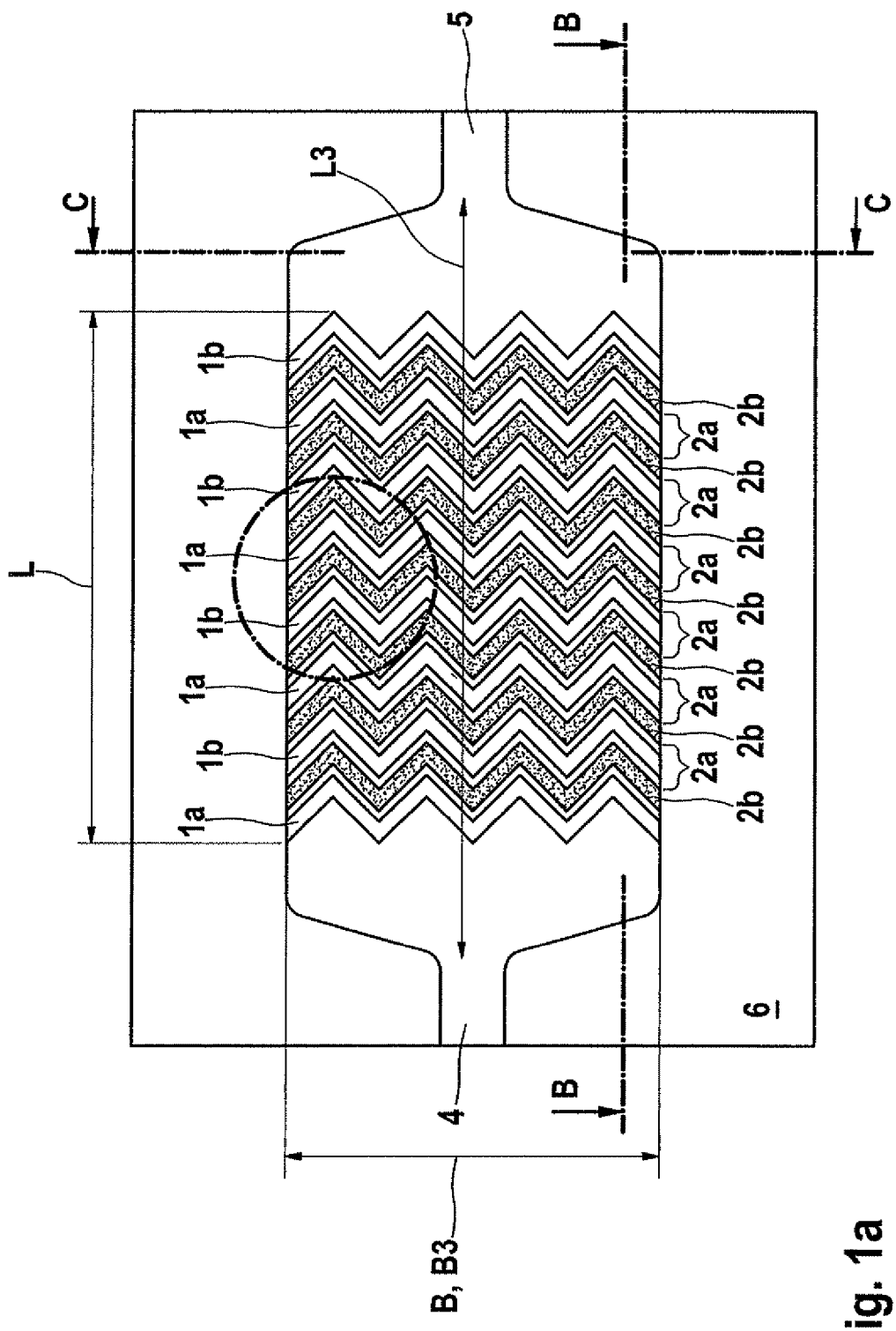
Fig. 1a (A - A)

(A - A)

(B - B)

(A - A)

(A - A)

(A - A)

(B - B)

(A - A)

(B - B)

(C - C)

MICROFLUIDIC CELL

RELATED APPLICATION INFORMATION

The present application claims priority to and the benefit of German patent application no. 10 2009 028 493.1, which was filed in Germany on Aug. 13, 2009, the disclosure of which is incorporated herein by reference.

FIELD OF THE INVENTION

The present invention relates to a microfluidic cell, a microfluidic system, use of the microfluidic cell and microfluidic system, and a method for separating, accumulating, and/or lysing polarizable bioparticles.

BACKGROUND INFORMATION

Microfluidic cells for the dielectrophoretic accumulation of bioparticles exist which have an interdigital electrode system. For the accumulation, an alternating voltage is applied to the interdigital electrode system, and a suspension containing bioparticles is pumped through the cell. The bioparticles may be collected on the interdigital electrode system by positive dielectrophoresis (pDEP), and the bioparticles may be repelled by negative dielectrophoresis (nDEP).

In Anal. Chem., 2007, 29, pages 1833-1839, Voldmann et al. describe several microfluidic cells having an interdigital electrode system on one side and a micromixer on the opposite side.

SUMMARY OF THE INVENTION

The subject matter of the exemplary embodiments and/or exemplary methods of the present invention is a microfluidic cell, in particular a flow cell, in particular for the dielectrophoretic separation and/or accumulation and/or lysis of polarizable bioparticles, for example bacteria and/or cells and/or viruses, the microfluidic cell including an interdigital electrode system composed of two electrode groups having interdigitated electrodes, and a micromixer having microchannels and microelevations. According to the exemplary embodiments and/or exemplary methods of the present invention, the interdigital electrode system and the micromixer are situated on the same side of the cell.

Using the microfluidic cell according to the present invention, polarizable bioparticles such as bacteria, cells, or viruses may be advantageously accumulated from a sample liquid flowing past and concentrated. A high yield of accumulated bioparticles and/or a high sample throughput, for example several milliliters of sample liquid within 30 to 60 minutes, may be achieved. The accumulated bioparticles may then optionally be lysed in the cell. The microfluidic cell may be advantageously integrated into a microfluidic "lab-on-a-chip" system. The flow in the region of the interdigital electrode system may be calmed due to the fact that the micromixer is situated on the same side of the cell as the interdigital electrode system. Accumulated bioparticles may thus be advantageously prevented from being washed out again during the accumulation.

An interdigital electrode system composed of two electrode groups having electrodes which are situated in an interdigitated manner may in particular be an electrode system composed of two comb-like/finger-like electrodes which are mutually engaged, in particular in an alternating manner ("interdigitated electrodes" (IDE)).

The interdigital electrode system and the micromixer may be situated on the bottom of the cell. The "bottom" of the cell may be understood to mean in particular the surface which in operating mode is situated at the bottom, in particular with respect to the direction of gravity.

In one specific embodiment of the present invention, electrodes of the interdigital electrode system are situated in the microchannels. In this way, the interdigital electrode system and the micromixer may advantageously form a combined interdigital electrode-micromixer system. Such a combined interdigital electrode-micromixer system may advantageously have a particularly good flow calming effect in the region of the electrodes of the interdigital electrode system. In particular, one electrode of the interdigital electrode system may be situated in each microchannel of the micromixer.

In another specific embodiment of the present invention, the electrodes of the interdigital electrode system and/or the microchannels and/or the microelevations are configured and situated in parallel.

In another specific embodiment of the present invention, the electrodes of the interdigital electrode system and/or the microchannels and/or the microelevations are configured and situated at an angle ($\alpha$) of $\geq 20°$ to $\leq 70°$, in particular of $\geq 40°$ to $\leq 50°$, with respect to the flow direction.

In another specific embodiment of the present invention, the electrodes of the interdigital electrode system and/or the microchannels and/or the microelevations are configured and situated in a zigzag shape, for example a zigzag shape having equal angles or a zigzag shape having unequal angles, in particular in the shape of a symmetrical or asymmetrical herringbone pattern, or in the shape of a parallel slash mark [/] pattern, in particular an equidistant parallel slash mark pattern.

In another specific embodiment of the present invention, the micromixer, in particular the microelevations of the micromixer, is/are made of an insulating material, for example a plastic or a polymer, for example a photoresist, a polycarbonate, or a solder resist. In this way the micromixer is advantageously able to alter the field distribution in the cell in such a way that a more efficient accumulation is made possible. For example, the field lines in the narrow sections of the cell may be focused, as the result of which additional inhomogeneity of the electrical field may be provided, and/or the dielectrophoretic force is able to act farther inside the cell.

In another specific embodiment of the present invention, the cell includes a flat electrode, in particular an electrode having a continuous/uninterrupted planar surface. The flat electrode may be situated on a side of the cell opposite from the side on which the interdigital electrode system and the micromixer are situated. In particular, the flat electrode may be situated opposite from the combined interdigital electrode-micromixer system. For example, the flat electrode may be situated on the cover of the cell. The "cover" of the cell may be understood in particular to mean the surface which in operating mode is situated at the top, in particular with respect to the direction of gravity. A flat electrode has the advantage that it is only roughly adjusted with respect to the interdigital electrode system, thus allowing the assembly of the cell to be simplified. The flat electrode may advantageously improve the accumulation efficiency of the cell, even if the flat electrode is kept by the voltage in a floating state during the accumulation. In addition, the flat electrode may improve the lysis. By applying an, in particular positive, voltage to the flat electrode, agglomerated bioparticles, in particular DNA, may be dislodged and moved toward the flat electrode, and thus to the central region of the cell. In this way the accumulated bioparticles may advantageously be better or more completely rinsed out.

The flat electrode may completely span the interdigital electrode system.

In another specific embodiment of the present invention, the surface area of the flat electrode essentially corresponds to the surface area of the interdigital electrode system, in particular the combined interdigital electrode-micromixer system. "Essentially" means that the surface areas may differ from one another by less than 10%.

The cell may have an inlet and an outlet. The interdigital electrode system and/or the micromixer, in particular the combined interdigital electrode-micromixer system, and/or the flat electrode may be situated in an area between the inlet and the outlet. The cell may be connected to a pump and/or to a sample inlet reservoir via the inlet. The outlet may be connected to a sample collection reservoir and/or to a waste reservoir.

In another specific embodiment of the present invention, the cell includes at least one further interdigital electrode system composed of two electrode groups having interdigitated electrodes, and/or one further micromixer having microchannels and microelevations, in particular a further combined interdigital electrode-micromixer-system. The further interdigital electrode system and/or the further micromixer, in particular the further combined interdigital electrode-micromixer system, may be spaced apart, for example by the distance from the previous interdigital electrode system and/or the previous micromixer, in particular the previous combined interdigital electrode-micromixer system. The further interdigital electrode system and/or the further micromixer, in particular the further combined interdigital electrode-micromixer system, may have a configuration which is different, in particular with regard to the shape and orientation, from the previous interdigital electrode system and/or the previous micromixer, in particular the previous combined interdigital electrode-micromixer system.

The micromixer and the interdigital electrode system, in particular the combined interdigital electrode-micromixer system, may have a length (L) of $\geq 10$ mm to $\leq 60$ mm, in particular of $\geq 20$ mm to $\leq 50$ mm, for example 40 mm, and/or a width (B) of $\geq 3$ mm to $\leq 30$ mm, in particular of $\geq 5$ mm to $\leq 10$ mm, for example 6 mm, and/or an area (L×B) of $\geq 30$ mm$^2$ to $\leq 1800$ mm$^2$, in particular $\geq 100$ mm$^2$ to $\leq 300$ mm$^2$, for example 6 mm×40 mm.

Distance (d) between two microchannels may be between $\geq 30$ μm and $\leq 500$ μm, in particular between $\geq 50$ μm and $\leq 200$ μm, for example 100 μm. In other words, the microelevations may have a width (B2$b$) of $\geq 30$ μm to $\leq 500$ μm, in particular of $\geq 50$ μm to $\leq 200$ μm, for example 100 μm. The microelevations may also have a height (H2) of $\geq 10$ μm to $\leq 400$ μm, in particular of $\geq 20$ μm to $\leq 50$ μm, for example 30 μm. In other words, the microchannels may have a depth (T2) of $\geq 10$ μm to $\leq 400$ μm, in particular of $\geq 20$ μm to $\leq 50$ μm, for example 30 μm. In addition, the microchannels may have a width (B2$a$) of $\geq 30$ μm to $\leq 800$ μm, in particular of $\geq 50$ μm to $\leq 300$ μm, for example 200 μm. Furthermore, the microchannels and/or the microelevations may have a length (L2) of $\geq 3$ mm to $\leq 30$ mm, in particular of $\geq 5$ mm to $\leq 10$ mm, for example 6 mm.

The electrodes of the interdigital electrode system may have a length (L1) of $\geq 3$ mm to $\leq 30$ mm, in particular of $\geq 5$ mm to $\leq 10$ mm, for example 6 mm, and/or a width (B1) of $\geq 10$ μm to $\leq 500$ μm, in particular of $\geq 50$ μm to $\leq 200$ μm, for example 100 μm or 200 μm, and/or a height (H1) of $\geq 0.1$ μm to $\leq 50$ μm, in particular of $\geq 20$ μm to $\leq 30$ μm, for example 25 μm. In addition, the electrodes of the interdigital electrode system may have a distance (D) to one another of $\geq 10$ μm to $\leq 500$ μm, in particular of $\geq 50$ μm to $\leq 200$ μm, for example 200 μm.

The cell may have a length (L3) of $\geq 10$ mm to $\leq 80$ mm, in particular of $\geq 20$ mm to $\leq 50$ mm, for example 40 mm, and/or a width (B3) of $\geq 3$ mm to $\leq 40$ mm, in particular of $\geq 5$ mm to $\leq 10$ mm, for example 6 mm, and/or a height (H3) of $\geq 20$ μm to $\leq 1000$ μm, in particular of $\geq 100$ μm to $\leq 200$ μm, for example 130 μm or 200 μm.

The flat electrode may have a length (L) of $\geq 10$ mm to $\leq 100$ mm, in particular of $\geq 20$ mm to $\leq 60$ mm, for example 40 mm, and/or a width (B) of $\geq 3$ mm to $\leq 50$ mm, in particular of $\geq 5$ mm to $\leq 105$ mm, for example 6 mm or 10 mm, and/or a height (H4) of $\geq 0.1$ μm to $\leq 50$ μm, in particular of $\geq 20$ μm to $\leq 30$ μm, for example 25 μm, and/or an area (L×B) of $\geq 30$ mm$^2$ to $\leq 1800$ mm$^2$, in particular of $\geq 100$ mm$^2$ to $\leq 300$ mm$^2$, for example 6 mm×40 mm.

For example, the ratio of height (H1) of the electrodes of the interdigital electrode system to height (H2) of the micromixer may be 1:2 to 1:100, and/or the ratio of height (H1) of the electrodes of the interdigital electrode system to height (H3) of the cell may be 1:10 to 1:1000, and/or the ratio of height (H2) of the micromixer to height (H3) of the cell may be 0.33:1 to 0.5:1.

The microfluidic cell may in particular be integrated into a microfluidic chip.

Moreover, the exemplary embodiments and/or exemplary methods of the present invention relates to a microfluidic system, for example a microfluidic chip, which includes a microfluidic cell according to the present invention.

A further subject matter of the exemplary embodiments and/or exemplary methods of the present invention is a method for the in particular dielectrophoretic separation and/or accumulation and/or lysis of polarizable bioparticles, for example bacteria and/or cells and/or viruses, using a microfluidic cell according to the present invention or a microfluidic system according to the present invention, which includes an accumulation phase, a high-frequency alternating voltage, for example of $\geq 30$ V to $\leq 50$ V, having a frequency of $\geq 0.5$ MHz to $\leq 1.5$ MHz, for example 1 MHz, being applied to the electrodes of the interdigital electrode system during the accumulation phase. A solution or suspension containing polarizable bioparticles, for example bacteria and/or cells and/or viruses, may be pumped through the microfluidic cell during the accumulation phase. When the cell has a flat electrode, the flat electrode may be kept by the voltage in a floating state during the accumulation phase. The flat electrode may be kept by the voltage in a floating state so it does not contact the flat electrode. In an electrical equivalent circuit diagram, this may be equivalent to a very high-impedance connection to ground having a (small) capacitor connected in parallel. As a result, a charge is able to build up on the flat electrode, and a voltage may develop. This voltage may be a function of the field conditions in the cell. The polarizable bioparticles may be released and/or collected at the end of the accumulation phase by switching off the alternating voltage. A concentration effect may be advantageously achieved in this way.

In another specific embodiment of the present invention, the method also includes a lysis phase, a low-frequency alternating voltage, for example of $\geq 30$ V to $\leq 50$ V, having a frequency of $\geq 1$ kHz to $\leq 20$ kHz, for example 10 kHz, being applied to the electrodes of the interdigital electrode system during the lysis phase. The pumps of the solution or suspension containing the polarizable bioparticles may be stopped during the lysis phase. When the cell has a flat electrode, the flat electrode may be kept in a floating state by the voltage also during the lysis phase. Following the lysis phase, the lysate may be rinsed out and/or reused.

In another specific embodiment of the present invention, in particular when the cell has a flat electrode, the method also includes a removal phase, in particular a DNA/RNA release phase, the electrodes of the interdigital electrode system being connected to ground, and a low-frequency alternating voltage or square wave voltage, for example of ≥50 mV to ≤150 mV, for example 100 mV, having a frequency of ≥0.1 Hz to ≤2 Hz, for example 1 Hz, and having a positive offset, for example of ≥10 mV to ≤100 mV, for example 50 mV, being applied to the flat electrode during the removal phase. Further polarizable bioparticles may be lysed in this phase. At the same time, as a result of the positive offset, negatively polarized bioparticles, for example DNA, may be moved toward the flat electrode.

The lysis phase and the removal phase may in particular be carried out simultaneously. This may be achieved, for example, by applying a low-frequency alternating voltage, for example of ≥30 V to ≤50 V, having a frequency of ≥1 kHz to ≤20 kHz, for example 10 kHz, to the electrodes of the interdigital electrode system, and applying a low-frequency alternating voltage or square wave voltage, for example of ≥50 mV to ≤150 mV, for example 100 mV, having a frequency of ≥0.1 Hz to ≤2 Hz, for example 1 Hz, and having a positive offset, for example of ≥10 mV to ≤100 mV, for example 50 mV, to the flat electrode.

Moreover, the exemplary embodiments and/or exemplary methods of the present invention relates to the manufacture of a microfluidic cell according to the present invention and/or a microfluidic system according to the present invention. A microfluidic cell according to the present invention or a microfluidic system according to the present invention may in particular be manufactured by microtechnology processes. For example, a plate-shaped substrate, for example a glass substrate, a silicon substrate, or a polymer substrate, in particular a Pyrex substrate, an SU-8 substrate, a Teflon substrate, or a PDMS substrate, or a substrate structured by injection molding, deep etching, or stamping, in particular hot stamping, for example a structured glass substrate, silicon substrate, or polymer substrate, in particular a Pyrex substrate, SU-8 substrate, Teflon substrate, or PDMS substrate, may be used. Electrodes may be attached thereto using thin-layer technology and/or lithography, for example. The resulting system may then be covered with a cap, for example a glass plate or a polymer plate, in particular a PDMS plate or a Pyrex plate.

Moreover, the exemplary embodiments and/or exemplary methods of the present invention relates to the use of a microfluidic cell according to the present invention and/or a microfluidic system according to the present invention in medical technology and microbiology, for example in medical analytics, in particular in an integrated microfluidic lab-on-a-chip system, for example for sample pretreatment, in particular for DNA and/or RNA analytics. For example, a lysate obtained using a cell according to the present invention or a system according to the present invention may be used for subsequent DNA or RNA analytics. In particular, pathogenic organisms may be concentrated prior to a subsequent analysis by using a cell according to the present invention or a system according to the present invention.

Further advantages and advantageous embodiments of the subject matters according to the exemplary embodiments and/or exemplary methods of the present invention are illustrated in the drawing and explained in the following description. It is pointed out that the drawing has only a descriptive character, and is not intended to limit the present invention in any way.

BRIEF DESCRIPTION OF THE DRAWINGS

FIG. 1a shows a schematic cross section, along line A-A, through a first specific embodiment of a microfluidic cell according to the present invention having a combined interdigital electrode-micromixer system.

FIG. 3b shows a schematic cross section, along line B-B, through the specific embodiment of a microfluidic cell according to the present invention shown in FIG. 3a.

DETAILED DESCRIPTION

Figure 1B:
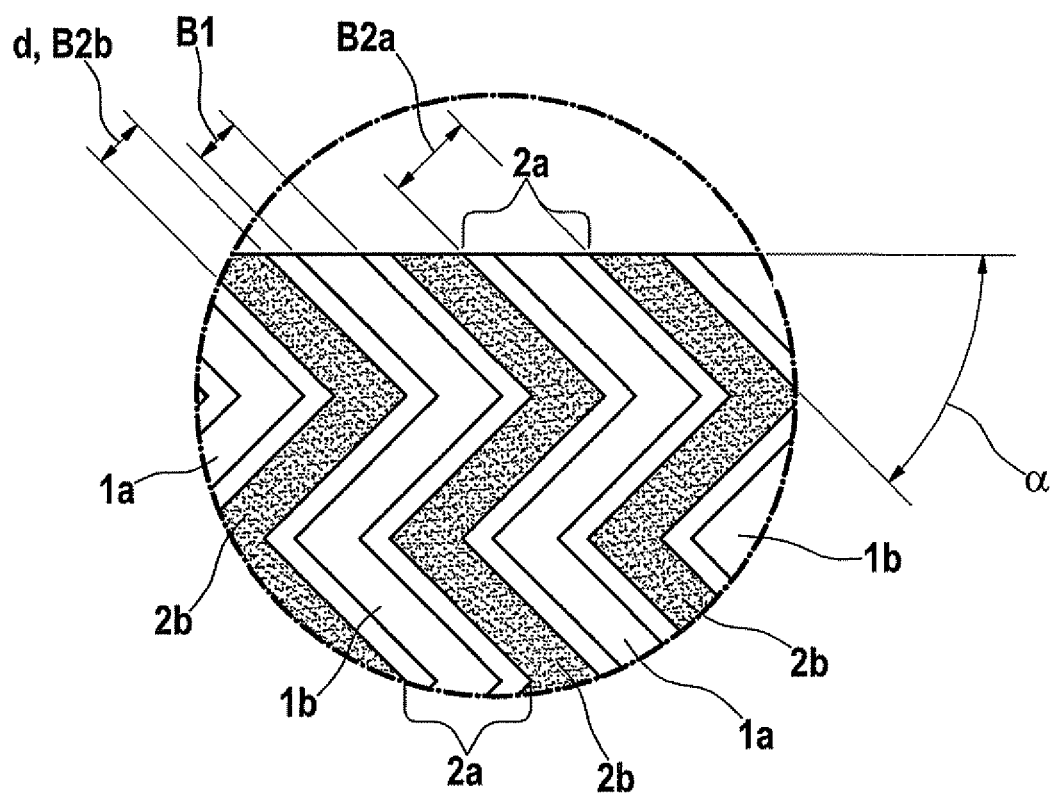
FIG. 1b shows a schematic enlarged view of the area shown in FIG. 1a and identified by a circle.

FIGS. 1a through 1d show a first specific embodiment of a microfluidic cell according to the present invention. FIGS. 1a through 1d also show that the microfluidic cell includes an interdigital electrode system composed of two electrode groups having interdigitated electrodes 1a, 1b, and a micromixer having microchannels 2a and microelevations 2b. According to the present invention, the interdigital electrode system and the micromixer are situated on the same side of the cell. FIGS. 1a through 1d also show that electrodes 1a, 1b of the interdigital electrode system are situated in microchannels 2a, and in this manner the interdigital electrode system and the micromixer form a combined interdigital electrode-micromixer system 1a, 1b, 2a, 2b. Electrodes 1a, 1b of the interdigital electrode system, microchannels 2a, and microelevations 2b are configured in a zigzag shape and oriented parallel to one another, in particular in the shape of a symmetrical herringbone pattern. Electrodes 1a, 1b of the interdigital electrode system, microchannels 2a, and microelevations 2b are oriented at an angle α of 45° with respect to the flow direction. FIGS. 1a through 1d also show that the cell has an inlet 4 and an outlet 5 and is integrated into a microfluidic chip 6.

Figure 1C:
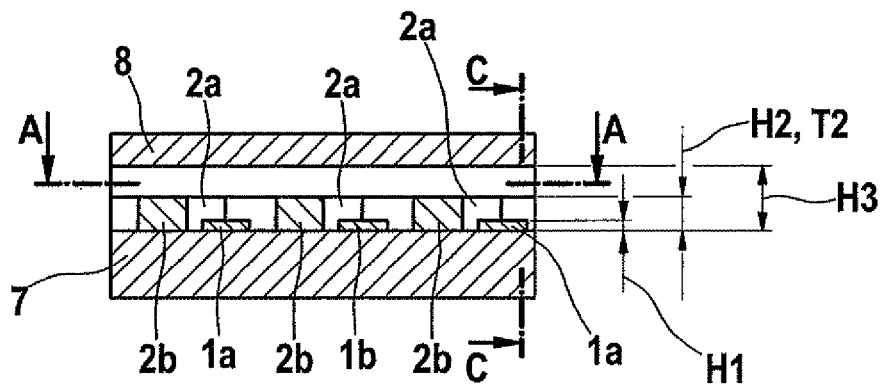
FIG. 1c shows a schematic cross section, along line B-B, through the specific embodiment of a microfluidic cell according to the present invention shown in FIGS. 1a and 1b.

FIG. 1c shows one specific embodiment of a microfluidic cell according to the present invention, having a structured (bottom) substrate 7 which is covered by a plate-shaped cap 8, thus forming a fluid channel. Height (H2) of the micromixer is approximately ⅓ to ½ of height (H3) of the cell. Height (H1) of the electrodes, in turn, is much smaller than height (H2) of the micromixer.

Figure 1D:
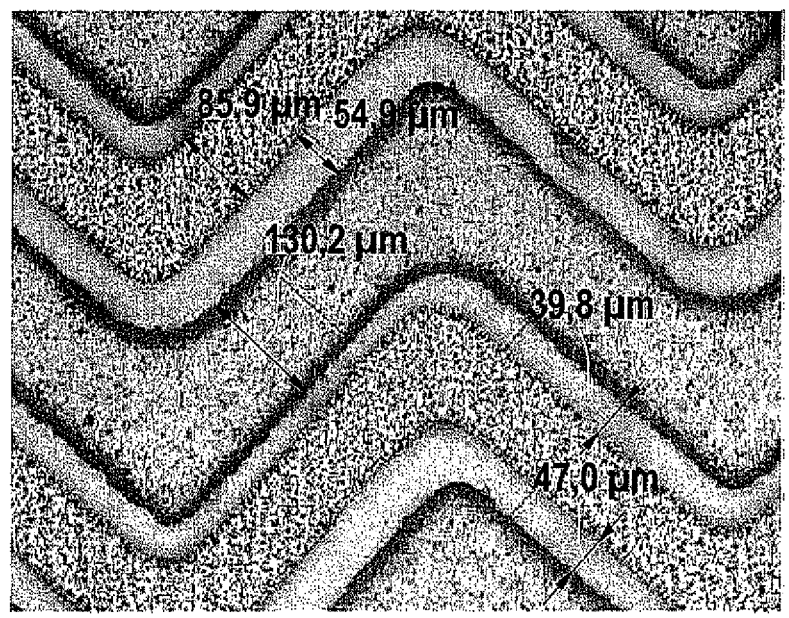
FIG. 1d shows a photograph of the combined interdigital electrode-micromixer system schematically shown in FIGS. 1a through 1c.

FIG. 1d shows a first implementation of the first specific embodiment using printed circuit board technology. The substrate, micromixer, and electrodes are composed of a printed circuit board, structured solder resist, and metallic printed conductors. The side walls of the channel are implemented using double-sided adhesive tape. A glass plate is used as the cover. The flat electrode of the similar third specific embodiment is implemented using a flat indium-tin oxide (ITO) plating for the cover.

Figure 2A:
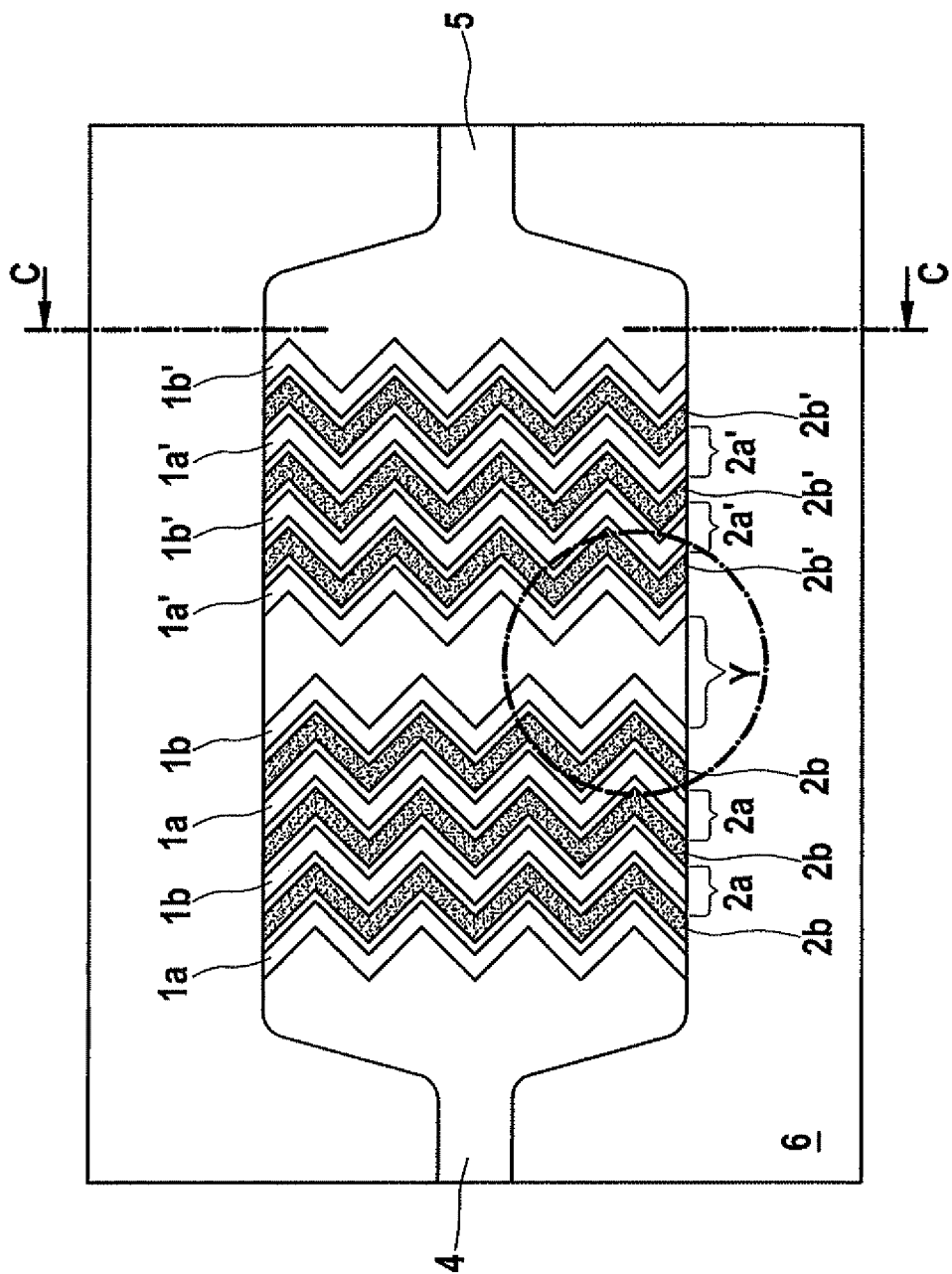
FIG. 2a shows a schematic cross section, along line A-A, through a second specific embodiment of a microfluidic cell according to the present invention having two interspaced, combined interdigital electrode-micromixer systems.
Figure 2B:
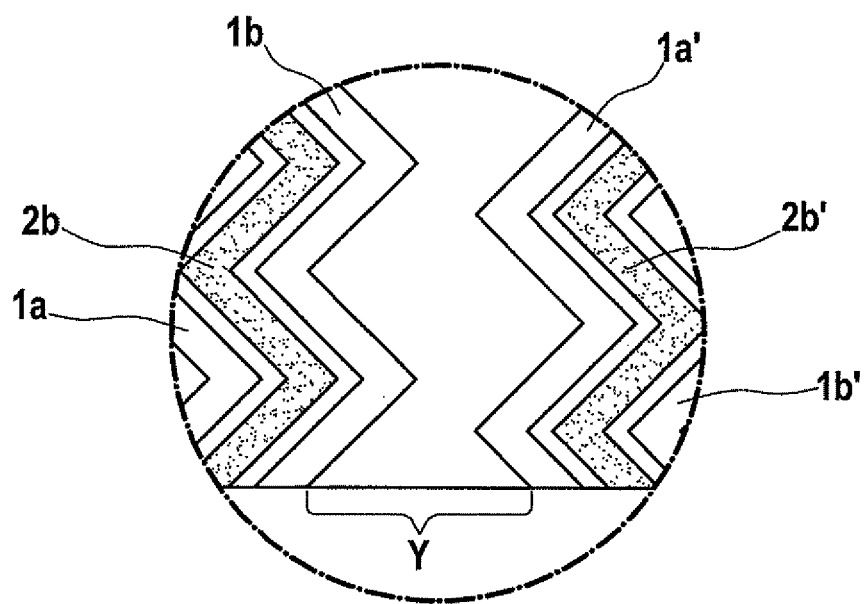
FIG. 2b shows a schematic enlarged view of the area shown in FIG. 2a and identified by a circle.

The second specific embodiment shown in FIGS. 2a and 2b differs from the first specific embodiment in that the microfluidic cell has two combined interdigital electrode-micromixer systems 1a, 1b, 2a, 2b; 1a', 1b', 2a', 2b' which are spaced apart by distance Y. FIGS. 2a and 2b show that the two combined interdigital electrode-micromixer systems 1a, 1b, 2a, 2b; 1a', 1b', 2a', 2b' differ by virtue of a different orientation. According to simulation, intermixture in the flow cell is further improved using this variant.

Figure 3A:
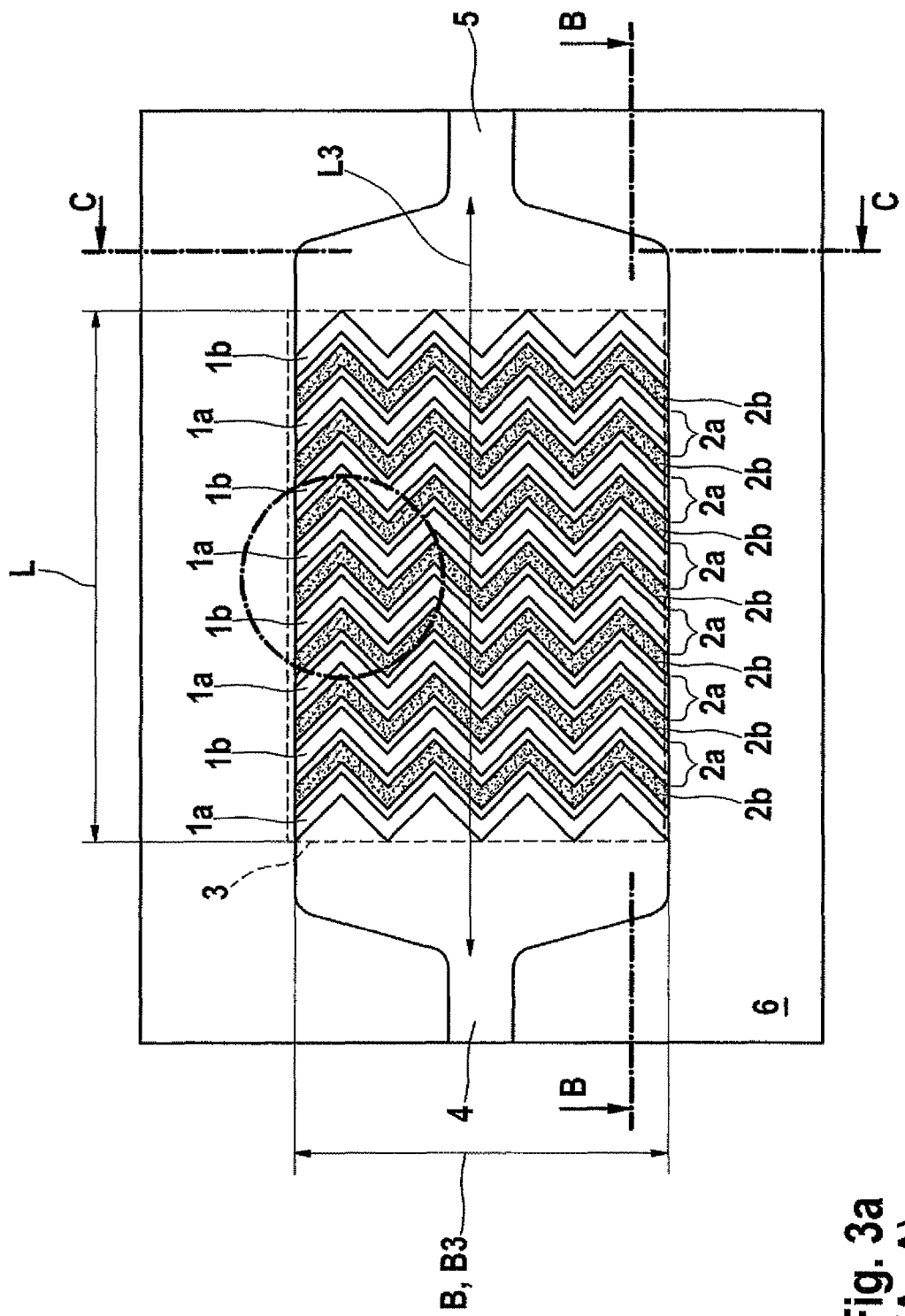
FIG. 3a shows a schematic cross section, along line A-A, through a third specific embodiment of a microfluidic cell according to the present invention having a combined interdigital electrode-micromixer system and a flat electrode.
Figure 3B:
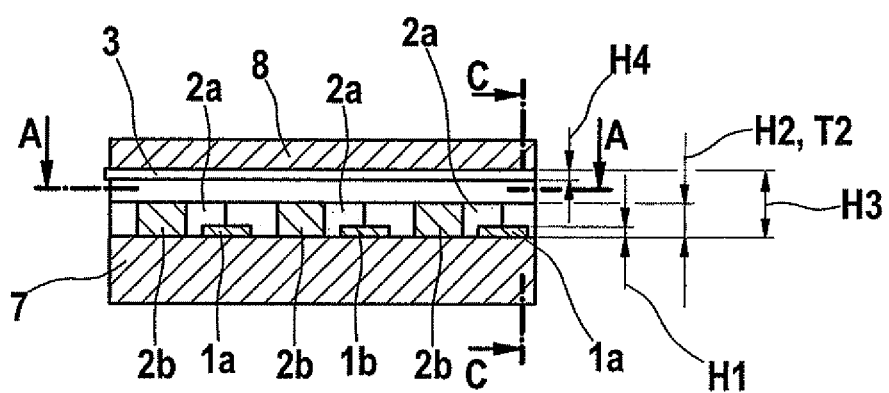

The third specific embodiment shown in FIGS. 3a and 3b differs from the first specific embodiment in that the microfluidic cell has a flat electrode 3 which is situated on a side of the cell which is opposite from the side on which interdigital electrode system 1a, 1b and micromixer 2a, 2b are situated. The flat electrode is mounted in particular on the bottom side of cap 8, and its dimensions essentially correspond to those of the active region of combined interdigital electrode-micromixer system 1a, 1b, 2a, 2b.

Figure 4:
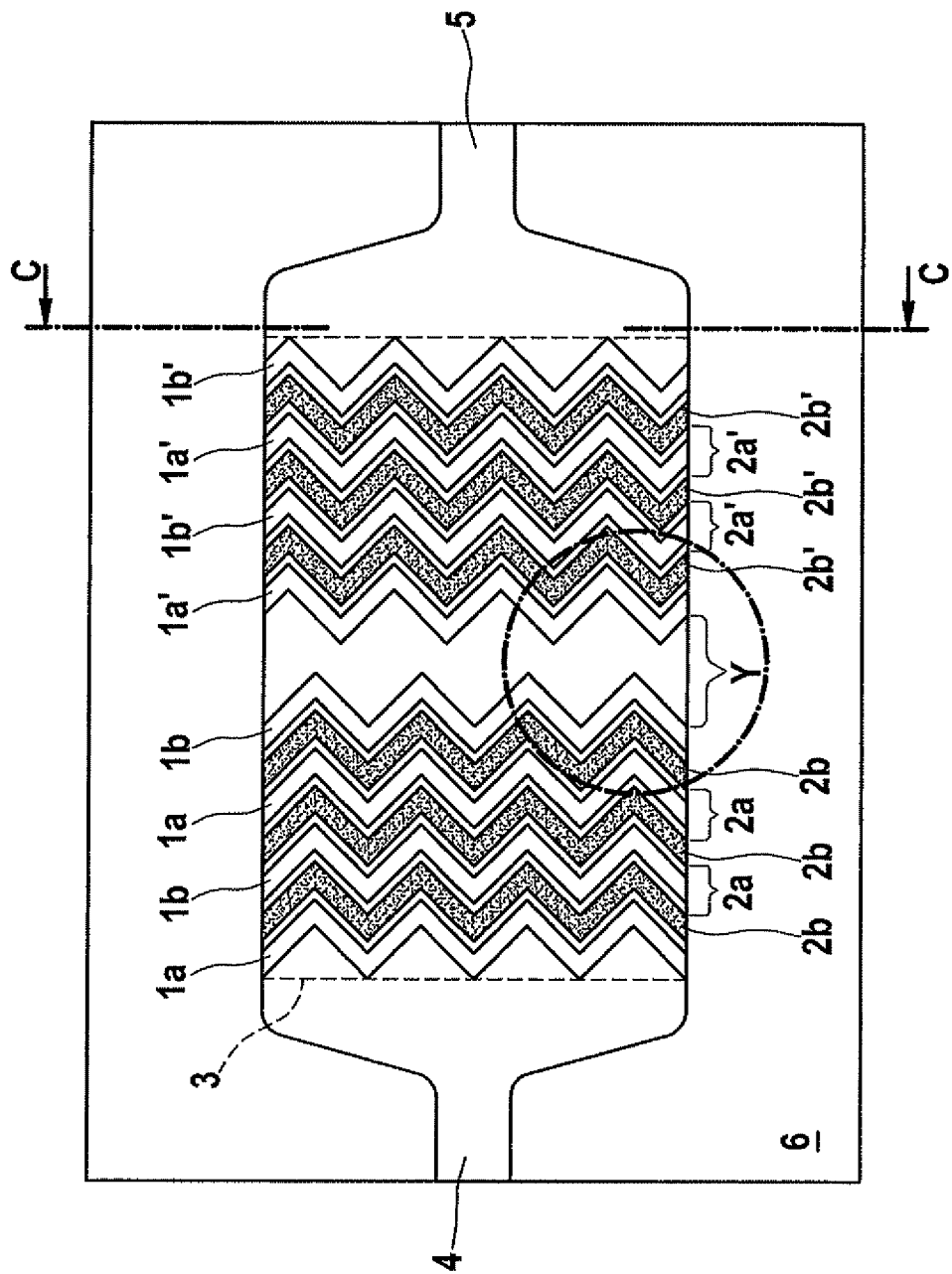
FIG. 4 shows a schematic cross section, along line A-A, through a fourth specific embodiment of a microfluidic cell according to the present invention having two interspaced, combined interdigital electrode-micromixer systems and a flat electrode.

The fourth specific embodiment shown in FIG. 4 differs from the first, second, and third specific embodiments in that the microfluidic cell has two combined interdigital electrode-micromixer systems 1a, 1b, 2a, 2b; 1a', 1b', 2a', 2b' which are spaced apart by distance Y, and a flat electrode 3 which is situated on a side of the cell which is opposite from the side on which combined interdigital electrode-micromixer systems 1a, 1b, 2a, 2b; 1a', 1b', 2a', 2b' are situated.

Figure 5:
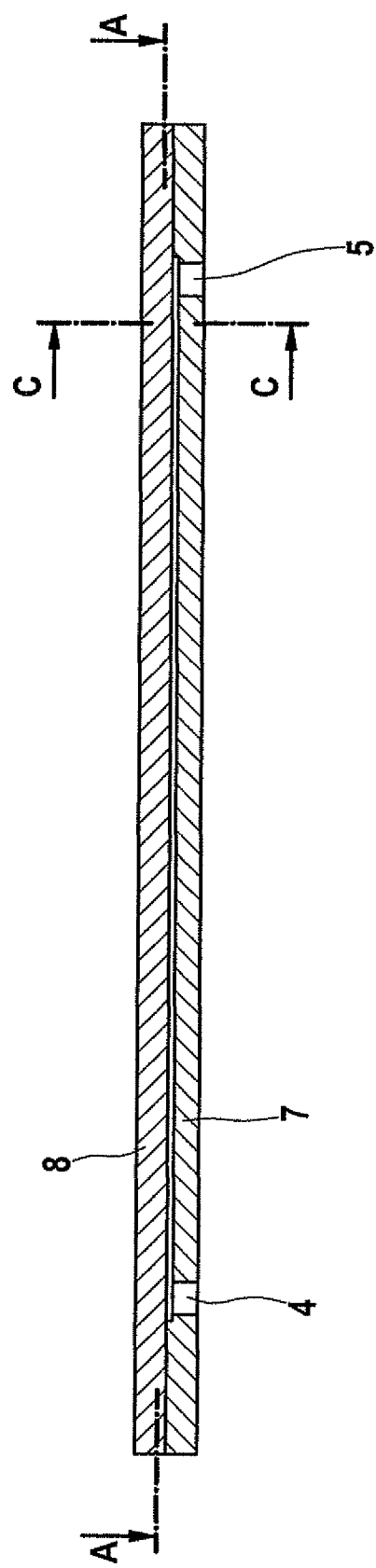
FIG. 5 shows a schematic cross section, along line B-B, through a fifth specific embodiment of a microfluidic cell according to the present invention in which the inlet and the outlet are integrated into the base plate.

FIG. 5 shows a schematic cross section, along line B-B, through a fifth specific embodiment of a microfluidic cell according to the present invention in which inlet 4 and outlet 5 are integrated into the base plate.

Figure 6A:
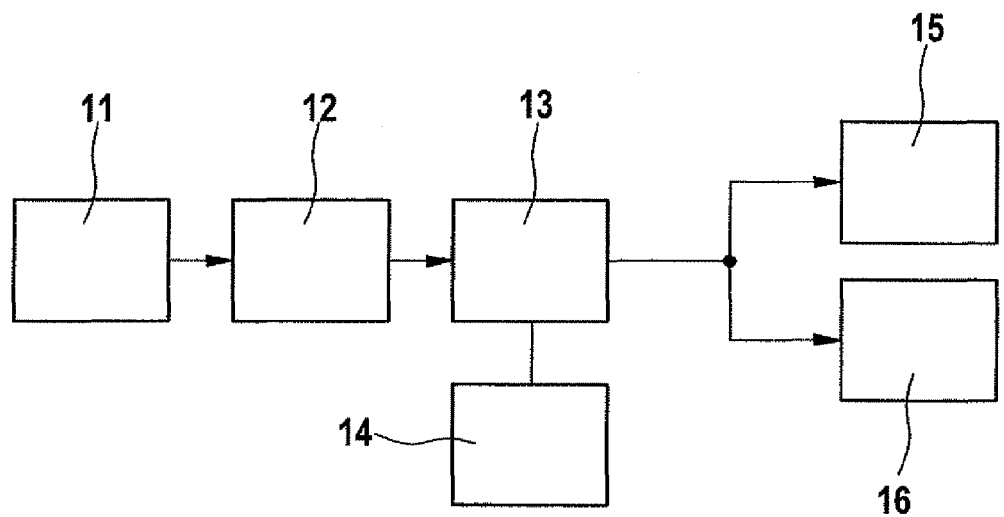
FIG. 6a shows a block diagram for illustrating one possible activation of a microfluidic cell according to the present invention.

FIG. 6a is a block diagram for illustrating one possible activation of one specific embodiment of a microfluidic cell according to the present invention. During the accumulation phase a polarizable solution or suspension containing bioparticles such as bacteria, cells, and/or viruses is pumped from sample reservoir 11, with the aid of pump 12, through a microfluidic chip 13 into which a microfluidic cell is integrated. A high-frequency alternating voltage, for example of 30 V and 50 V and having a frequency of 1 MHz, is applied to electrodes 1a, 1b of the interdigital electrode system, adjacent electrodes 1a, 1b of the interdigital electrode system in each case having opposite polarities. The accumulation then takes place between electrodes 1a, 1b of the interdigital electrode system. Outlet 5, which in principle may be connected to a sample collection reservoir 15 and to a waste reservoir 16, is connected to waste reservoir 16.

During the lysis phase, pump 12 is first switched off. The polarizable bioparticles are then lysed by lowering the frequency of the alternating voltage at electrodes 1a, 1b of the interdigital electrode system to a low-frequency range, for example to 10 kHz.

In conclusion, the lysate is rinsed out and may be reused.

In a microfluidic cell according to the third or fourth specific embodiment, the voltage at flat electrode 3 may be kept in a floating state during the accumulation phase. After the lysis phase, an alternating voltage or square wave voltage, for example of 100 mV and having a frequency of 1 Hz, and having a positive offset, for example of 50 mV, may then be applied between flat electrode 3 and electrodes 1a, 1b of the interdigital electrode system. Further polarizable bioparticles may be lysed in this phase. At the same time, as a result of the positive offset voltage, for example, negatively charged DNA may be drawn from combined interdigital electrode-micromixer system 1a, 1b, 2a, 2b toward the center of the cell channel.

Figure 6B:
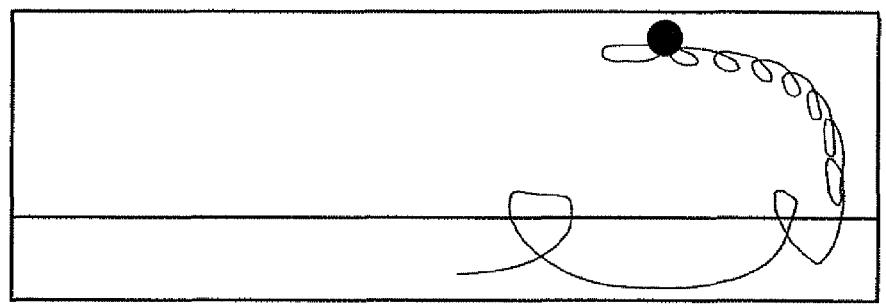
FIG. 6b shows a schematic cross-sectional illustration of the result of a flow simulation for a microfluidic cell having a combined interdigital electrode-micromixer system, along line C-C.

FIG. 6b shows the result of a flow simulation of a path of a polarizable bioparticle through the first specific embodiment of the microfluidic cell, in a viewing direction from outlet 5 to inlet 4. The dot denotes the region at which the polarizable bioparticle enters the cell. FIG. 6b illustrates that combined interdigital electrode-micromixer system 1a, 1b, 2a, 2b causes swirling, circulation, and intermixture of the cell volume. As a result, polarizable bioparticles which enter the cell at a distance from electrodes 1a, 1b of the interdigital electrode system also reach the vicinity of electrodes 1a, 1b of the interdigital electrode system on their path through the cell, and at that location are intercepted by the electrical field. The flow simulations also show that the micromixer causes calming of the flow at the bottom of the cell. Accumulated bioparticles may thus be advantageously prevented from being washed away at electrodes 1a, 1b of the interdigital electrode system.

Figure 7A:
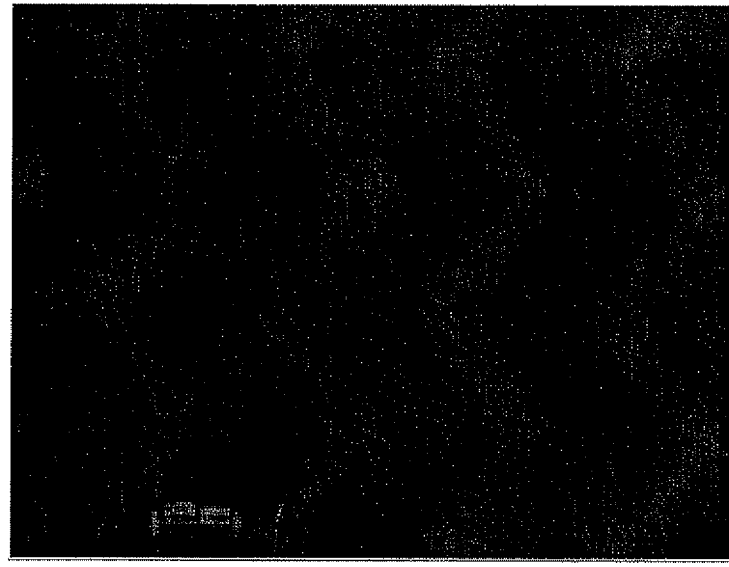
FIG. 7a shows a photograph of lysed fluorescent *E. coli* bacteria in a microfluidic cell according to the first specific embodiment.
Figure 7B:
FIG. 7b shows a photograph of lysed fluorescent *E. coli* bacteria in a microfluidic cell according to the third specific embodiment.

FIGS. 7a and 7b show that, using a microfluidic cell according to the first specific embodiment as well as a microfluidic cell of the third specific embodiment, E. coli bacteria in deionized water may be accumulated at flow rates between 13 mL/min and 300 mL/min and lysed. Propidium iodide was used as stain. A comparison of FIGS. 7a and 7b also shows that the intensity of fluorescence is markedly increased in the third specific embodiment having flat electrode 3. This is attributed to the fact that, first, the lysis efficiency may be improved using flat electrode 3, and second, DNA may be removed from electrodes 1a, 1b of the interdigital electrode system as a result of the additional applied voltage.

What is claimed is:

1. A method for at least one of separating and accumulating polarizable bioparticles, the method comprising:
using a microfluidic cell, including:
an interdigital electrode system composed of two electrode groups having interdigitated electrodes;
a micromixer having microchannels and microelevations; and
a flat electrode situated on a side of a cell opposite from the side on which the interdigital electrode system and the micromixer are situated;
wherein the interdigital electrode system and the micromixer are situated on a same side of the cell;

performing an accumulation phase, wherein a high-frequency alternating voltage is applied to the electrodes of the interdigital electrode system during the accumulation phase calming a flow of bioparticles in a region of the interdigital electrode system using the micromixer;

inhibiting a washing out of the bioparticles in the region of the interdigital electrode system using the micromixer; and performing at least one of the following: (i) a lysis phase, wherein a low-frequency alternating voltage is applied to the interdigital electrodes, and (ii) a removal phase, wherein a low-frequency or square wave voltage is applied between the interdigital electrode system and the flat electrode;

wherein the lysis phase and the removal phase are performed simultaneously by applying the low-frequency alternating voltage.

2. The method of claim 1, wherein electrodes of the interdigital electrode system are situated in the microchannels and form a combined interdigital electrode-micromixer system.

3. The method of claim 1, wherein the electrodes of at least one of the interdigital electrode system, the microchannels, the microelevations are configured and situated in parallel.

4. The method of claim 1, wherein the electrodes of at least one of the interdigital electrode system, the microchannels, the microelevations are configured and situated at an angle ($\alpha$) of $\geq 20°$ to $\leq 70°$ with respect to a flow direction.

5. The method of claim 1, wherein the electrodes of at least one of the interdigital electrode system, the microchannels, the microelevations are configured and situated in one of a zigzag shape and in a parallel slash mark [/] pattern shape.

6. The method of claim 1, wherein the micromixer is made of an insulating material.

7. The method of claim 1, wherein the surface area of the flat electrode essentially corresponds to the surface area of the combined interdigital electrode-micromixer system.

8. The method of claim 1, wherein the cell includes at least one of (i) at least one further interdigital electrode system composed of two electrode groups having interdigitated electrodes, and (ii) a further micromixer having microchannels and microelevations.

9. The method of claim 1, wherein at least one of the following is satisfied:

the combined interdigital electrode-micromixer system has a length of $\geq 10$ mm to $\leq 60$ mm, the combined interdigital electrode-micromixer system has a width of $\geq 3$ mm to $\leq 30$ mm, the combined interdigital electrode-micromixer system has an area of $\geq 30$ mm$^2$ to $\leq 1800$ mm$^2$, the microchannels and/or the microelevations have a length of $\geq 3$ mm to $\leq 30$ mm, the distance between two microchannels is between $\geq 30$ µm and $\leq 500$ µm, the microchannels have a width of $\geq 30$ µm to $\leq 800$ µm, the microelevations have a width of $\geq 30$ µm to $\leq 500$ µm, the microelevations have a height of $\geq 10$ µm to $\leq 400$ µm, the microchannels have a depth of $\geq 10$ µm to $\leq 400$ µm, the electrodes of the interdigital electrode system have a length of $\geq 3$ mm to $\leq 30$ mm, the electrodes of the interdigital electrode system have a width of $\geq 10$ µm to $\leq 500$ µm, the electrodes of the interdigital electrode system have a height of $\geq 0.1$ µm to $\leq 50$ µm, the electrodes of the interdigital electrode system have a distance to one another of $\geq 10$ µm to $\leq 500$ µm, the cell has a length, the cell has a width of $\geq 3$ mm to $\leq 40$ mm, the cell has a height of $\geq 20$ µm to $\leq 1000$ µm, the flat electrode has a length of $\geq 10$ mm to $\leq 100$ mm, the flat electrode has a width of $\geq 3$ mm to $\leq 50$ mm, the flat electrode has a height of $\geq 0.1$ µm to $\leq 50$ µm, and the flat electrode has an area of $\geq 30$ mm$^2$ to $\leq 1800$ mm$^2$.

10. The method of claim 1, further comprising:

performing the lysis phase, wherein the low-frequency alternating voltage is applied to the electrodes of the interdigital electrode system during the lysis phase.

11. The method of claim 1, further comprising:

performing the removal phase, wherein the electrodes of the interdigital electrode system are connected to ground, and wherein one of the low-frequency alternating voltage and a square wave voltage having a positive offset is applied to a flat electrode during the removal phase, the flat electrode situated on a side of the cell opposite from the side on which the interdigital electrode system and the micromixer are situated.

12. The method of claim 1, wherein the microfluidic cell is a flow cell for at least one of dielectrophoretic separation, accumulation, and lysis of polarizable bioparticles.

13. The method of claim 1, wherein the microfluidic cell is a flow cell for at least one of dielectrophoretic separation, accumulation, and lysis of polarizable bioparticles, which includes at least one of bacteria, cells and viruses.

14. The method of claim 1, wherein an alternating voltage is applied to the electrodes in the interdigital electrode system.

15. The method of claim 1, wherein the high-frequency alternating voltage is applied during the accumulation phase such that adjacent electrodes in the interdigital electrode system have opposite polarities.

16. The method of claim 1, wherein the flat electrode has a continuous and uninterrupted planar surface.

* * * * *